(12) United States Patent
Suda et al.

(10) Patent No.: US 8,062,671 B2
(45) Date of Patent: *Nov. 22, 2011

(54) OILY SKIN PREPARATION FOR EXTERNAL USE

(75) Inventors: Yukimitsu Suda, Yokohama (JP); Mari Yoshida, Yokohama (JP); Eriko Kawai, Yokohama (JP); Shigeru Mugikura, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 1086 days.

This patent is subject to a terminal disclaimer.

(21) Appl. No.: 10/540,632

(22) PCT Filed: Dec. 26, 2003

(86) PCT No.: PCT/JP03/16952
§ 371 (c)(1),
(2), (4) Date: Jun. 23, 2005

(87) PCT Pub. No.: WO2004/060340
PCT Pub. Date: Jul. 22, 2004

(65) Prior Publication Data
US 2006/0110414 A1  May 25, 2006

(51) Int. Cl.
*A61K 9/16* (2006.01)
*A61K 8/02* (2006.01)
*A61K 9/50* (2006.01)

(52) U.S. Cl. ........................ 424/490; 424/401

(58) Field of Classification Search ............ 424/490, 424/401
See application file for complete search history.

(56) References Cited

U.S. PATENT DOCUMENTS

| | | | | |
|---|---|---|---|---|
| 5,015,469 A * | 5/1991 | Yoneyama et al. | ............ | 424/59 |
| 5,061,481 A * | 10/1991 | Suzuki et al. | ............ | 424/63 |
| 5,118,496 A * | 6/1992 | Herstein | ............ | 424/63 |
| 5,122,418 A * | 6/1992 | Nakane et al. | ............ | 424/401 |
| 5,182,103 A * | 1/1993 | Nakane et al. | ............ | 424/78.03 |
| 5,219,560 A * | 6/1993 | Suzuki et al. | ............ | 424/63 |
| 5,578,311 A * | 11/1996 | Nagatani et al. | ............ | 424/401 |
| 5,928,658 A * | 7/1999 | Kishida et al. | ............ | 424/401 |
| 5,928,660 A * | 7/1999 | Kobayashi et al. | ............ | 424/401 |
| 5,968,531 A | 10/1999 | Miyoshi et al. | | |
| 6,080,430 A * | 6/2000 | Ogawa et al. | ............ | 424/490 |
| 6,649,179 B2 * | 11/2003 | Yoshida et al. | ............ | 424/401 |
| 2005/0181067 A1 * | 8/2005 | Yokoyama et al. | ............ | 424/641 |

FOREIGN PATENT DOCUMENTS

| EP | 1112744 A1 | 7/2001 |
|---|---|---|
| WO | PCT/US98/24257 | 5/2000 |

OTHER PUBLICATIONS

Japanese Patent Abstract Publication No. 09-315926 published Dec. 9, 1997, two pages.
Japanese Patent Abstract Publication No. 11-130652 published May 18, 1999.
Japanese Patent Abstract Publication No. 2003-012491 published Jan. 15, 2003.
Supplementary European Search Report for EP 03782945 dated Feb. 2, 2006, two pages.
Japanese Patent Abstract Publication No. 01190625 published Jul. 31, 1989, one page.

* cited by examiner

*Primary Examiner* — Rebecca Prouty
*Assistant Examiner* — Danielle Sullivan
(74) *Attorney, Agent, or Firm* — Rankin, Hill & Clark LLP

(57) ABSTRACT

The objective of this invention is to provide an oily external composition for skin having an excellent rough skin recovering/preventing effect, and wherein powder is well dispersed in oil. An oily external composition for skin of this invention is characterized in that comprising a complex powder (the surface of lipophilic base powder is covered with zinc oxide) and an oil component, wherein said complex powder is dispersed in said oil component, and wherein zeta-potential of said lipophilic base powder is negative value at pH on skin. It is preferable that zeta-potential of said lipophilic base powder is −10 mV or less at pH on skin. It is preferable that said lipophilic base powder is swelled in the condition of dispersing in oil. Above-mentioned external composition can be used as a rough skin recovering composition and a sensitive skin caring composition.

7 Claims, 2 Drawing Sheets

OILY SKIN PREPARATION FOR EXTERNAL USE

RELATED APPLICATIONS

This application claims priority to the Japanese Patent Application 2002-381343 dated on Dec. 27, 2002 is hereby incorporated with reference for all purposes.

BACKGROUND OF THE INVENTION

1. Field of the Invention

The present invention relates to an oily external composition for skin, and in particular, the oily external composition for skin containing zinc oxide complex powder.

2. Prior Art

Conventionally, for protecting skin from ultraviolet rays, some powders such as zinc oxide and titanium dioxide are added in oily external composition for skin. It is difficult to disperse these inorganic powders in oil base, because the surface of said powders generally has hydrophilic property. Concerning emulsion cosmetics (a surfactant is added to oil phase containing powder, and water phase is added to therein and emulsified), sometimes aggregation occurs due to interaction among powder, surfactant and water. As a result, the composition lacks its stability and the functions of powder itself are not shown fully.

For the purpose of improving dispersibility of powder, many kinds of cosmetic compositions are developed; such as cosmetics comprising lipophilic powder whose surface is hydrophobicized [for example complex powder that zinc oxide is covered with magnesium aluminate metasilicate (Japanese Patent Publication Hei 1-308819), cosmetics comprising complex powder that zinc oxide is covered with fluorine modified silicone (Japanese Patent Publication Hei 7-277914)] and cosmetics that powder is disperses in oil dispersion medium with particular dispersant (Japanese Patent Publication Hei 9-208438).

In the above cosmetics, although dispersibility of powder in oil is improved to some extent, it is not enough. And it is difficult to exhibit function that zinc oxide itself originally owns, because its surface is covered fully.

SUMMARY OF THE INVENTION

This invention is established on the basis of the above problems and its objective is to provide an oily external composition for skin having an excellent rough skin recovering/preventing effect, and wherein powder is well dispersed in oil.

As a result of diligent studies for achieving the object, it is found out that a particular complex powder (that the surface of lipophilic base powder is covered with zinc oxide), is well dispersed in oil, and adsorbs and inactivates plasminogen activator on surface of skin. Therefore it has also excellent rough skin recovering/preventing effect to various skin diseases and rough skin accompanied with a change in activity of plasminogen activating enzyme, which resulted in completion of the present invention.

Namely an oily external composition for skin of this invention is characterized in that comprising complex powder that the surface of lipophilic base powder is covered with zinc oxide and an oil component, wherein said complex powder is dispersed in said oil component, and wherein zeta-potential of said lipophilic base powder is negative value at pH on skin.

It is preferable that zeta-potential of said lipophilic base powder is −10 mV or less at pH on skin.

As the above-mentioned oily external composition for skin, it is preferable that the covering rate of zinc oxide is the range of 1 to 90% relative to the surface of lipophilic base powder in the condition of dispersing in oil.

It is preferable that said lipophilic base powder is swelled in the condition of dispersing in oil.

As the above-mentioned oily external composition for skin, it is preferable that said lipophilic base powder is an organic powder, especially one or more powder selected from the group of silicone resin, silicone rubber, silicone resin-covered-silicone rubber, polyamide, polymethyl methacrylate and ethyl carbamate.

Also, it is preferable that silicone oil is comprised in the oily external composition for skin as oil component. It is preferable that the content of said complex powder is the range of 1 to 50% by weight.

The above-mentioned external composition can be used as a rough skin recovering composition and a sensitive skin caring composition.

Figure 1:
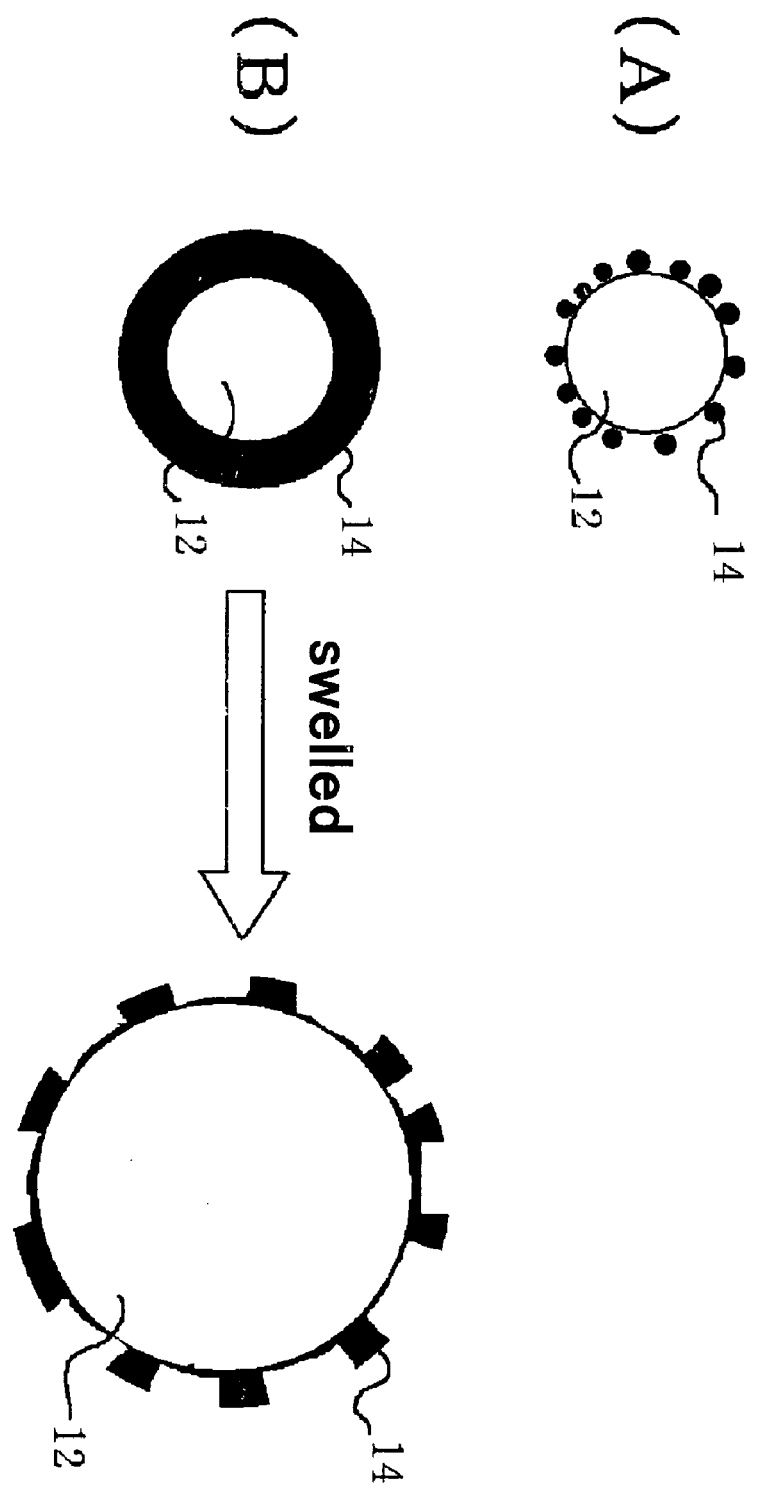
FIG. 1 shows the complex powder according to this invention.

Lipophilic base powder
Zinc oxide
Rotating container
Powder raw material
Inner piece

DETAILED DESCRIPTION OF THE PREFERRED EMBODIMENT

Preferable embodiments of the present invention are explained below.

Complex Powder

Rough Skin Recovering and Preventing Effect

In recent years, it is revealed that the activity-change of protease (especially fibrinolytic enzymes such as plasmin and plasminogen activator) is deeply involved in clinical picture formation of various skin diseases accompanied with rough skin or keratinization abnormality. For example, it is reported that the distribution change of plasmin is recognized in an epidermal cell layer in which rough skin is caused experimentally, and that an anti-plasmin agent is effective for preventing/recovering rough skin (Kenji Kitamura: J. Soc. Cosmet. Chem. Jpn; 29(2), 1995). Plasminogen activator is a protease that specifically acts on plasminogen (precursor of plasmin) and converts it into active plasmin In addition, high fibrinogenolytic activity in epidermis is recognized about atopic dermatitis (T. Lotti: Department of Dermatology; 28 (7), 1989). Further, about psoriasis (a representative of inflammatory abnormality keratinizing diseases), it is reported that the plasminogen activator activity is high in its affected part epidermis (Haustein: Arch. Klin. Exp. Dermatol; 234, 1969), and that plasminogen activator is extracted from psoriasis squama using high-concentrated salt solution (Fraki, Hopsu-Havu: Arch. Dermatol. Res; 256, 1976).

The complex powder of this invention is that base powder and zinc oxide are combined. The base powder adsorbs plasminogen activator and zinc oxide elutes zinc ion, and said zinc ion inhibits the activity of plasminogen activator. Therefore the complex powder of this invention is excellent in rough skin recovering/preventing effect, Zinc oxide. About the complex powder of this invention, zinc oxide elutes zinc ion and inactivates plasminogen activator. The blocking rates of urokinase (UK) of various ions at ion concentration 100 ppm are shown in the following Table 1. UK is a kind of plasminogen activator.

Measuring method of UK blocking rate. A Tris-HCl buffer (pH7.5) is added to 20 μL of sample suspension, to give total amount of 180 4-20 μL of 300 U/mL active type UK is added thereto and left 30 minutes at room temperature. Thereafter, 20 μL of S2444 [(CHROMOGENIX) which is a specific synthetic substrate for UK] is added thereto and left in thermostat (37° C.) for 30 minutes. Thereafter, 20 μL of 12% trichloroacetic acid solution is added to stop the reaction, and powder is filtered. Absorbance of the filtrate at 405 nm is measured to obtain UK activity in an assessment system and UK blocking rate of the sample is calculated.

TABLE 1

| Sample | UK blocking rate (%) |
|---|---|
| $Zn^{2+}$ | 52 |
| $Zr^{4+}$ | 45 |
| $Cu^{2+}$ | 36 |
| $Ni^{2+}$ | 30 |
| $Co^{2+}$ | 27 |
| $Al^{3+}$ | 16 |
| $Ce^{3+}$ | 5 |
| $Na^+, Li^+, K^+, Mn^{2+}, Ba^{2+}, Mg^{2+}, Ba^{2+}, Ca^{2+}$ | 0 |

As shown in Table 1, it is confirmed that zinc ion has the most excellent UK blocking activity. There is high specificity in the operation of each ion to the enzyme.

In the present invention, although complex powder is dispersed in oil, plasminogen activator inhibiting action can be shown. It is because the complex powder is contacted with water phase in cosmetic and zinc ion elutes from zinc oxide.

Alternatively, plasminogen activator inhibiting action can also be shown even in cosmetic not containing water, because zinc ion is dissolved out from zinc oxide by moisture on skin at applying.

Zinc oxide is listed in Japanese Pharmacopoeia. Zinc oxide is known to be combined with skin protein to form a film, and shows its pharmacological actions (astringent action, anti-inflammatory action and protecting action).

However, as long as the inventors know, there is no report showing the fact that zinc oxide adsorbs enzyme on skin and operates to its activity. In this invention, it is desirable that the average primary particle size of zinc oxide is 0.01 to 500 μm, although not restricted this range.

Lipophilic base powder. In this invention, it is preferable that the zeta-potential of lipophilic base powder is negative value (especially −10 mV or less) at pH on skin in order to adsorb plasminogen activator whose zeta-potential is positive value.

When a powder has an electric charge in liquid, an ion having the opposite electric charge is attracted to said powder by static electricity power in order to compensate the electric charge, so an electric double layer is produced. The outermost potential of the double layer is called zeta-potential. Accordingly, the zeta-potential is used preferably in evaluating the surface charge condition of an object, and it enables to evaluate an ability of adsorbing an enzyme electrically. The zeta-potential can be obtained in accordance with the Smoluchowski's formula:

$$\text{Zeta-potential} = 4\pi\eta U/\in$$

(in the above formula, η is the viscosity of the solvent, U is the electrophoresis mobility, $\in$ is the dielectric constant of the solvent).

In order to obtain zeta-potential, an electrophoresis is employed to measure the velocity of the colloidal particle (V) and the electrophoresis mobility (U). Under the electric field (E), the charged colloidal particle moves. V is obtained by the formula: V=L/t (wherein L is the distance of the movement and t is the time), and U is obtained by the formula: U=V/E.

Measuring method of zeta-potential. A sample is dispersed in Tris-HCl buffer of pH 7.5, subjected to ultrasonic treatment, and used for measurement. The zeta-potential is measured by electrophoresis light scattering photometer LEZA-600 (manufactured by Otsuka Electronics Co., Ltd). Measurement is performed three times, and the result is expressed as an average value thereof.

A relationship between the zeta-potential of main substance (at pH 7.5) and UK adsorbing rate (at the concentration of 100 ppm) are shown in the following Table 2.

Measuring method of the UK adsorbing rate. Tris-HCl buffer (pH 7.4) is added to 20 μl of sample suspension to give total amount of 180 μl, 20 μl of precursor type urokinase solution (10 μg/ml) is added therein and left for 5 minutes at room temperature. And the sample powder is filtered and the filtrate is collected. The sample powder is washed sufficiently with constant amount of Tris-HCl buffer, said buffer is added to the filtrate, and this is used as the non-adsorbent urokinase solution. The concentration of UK in said non-adsorbent urokinase solution is determined by the ELISA method using TintElize uPA (biopool). From the value of concentration of UK, calculating the amount of the urokinase adsorbed on the sample powder, UK adsorbing rate is obtained.

TABLE 2

| Sample | Zeta-potential (mV) | UK adsorbing rate (%) |
|---|---|---|
| Polyamide (Nylon SP500 ™) | −32.0 | 34 |
| Polymethyl methacrylate (Ganzpearl ™) | −18.0 | 42 |
| Silicone resin (Tospearl 145A ™) | −14.0 | 30 |
| Silicone rubber (Trefil E506W ™) | −12.0 | 18 |
| Ethyl carbamate (Plastic powder ™) | −13.0 | 27 |
| Organo polysiloxane extremer spherical powder (Trefil E506S ™) | −12.0 | 18 |
| Cellulose (Celluflow C-25 ™) | −2.0 | 21 |
| Polyethylene (Flo-thene UF ™) | +1.0 | 10 |

Shown in Table 2, there is a relationship between zeta-potential and UK adsorption rate. There is a tendency that as zeta-potential is low, UK adsorption rate is higher, although it is not necessarily proportional relationship.

Therefore it is preferable that zeta-potential of lipophilic base powder of this invention is −10 mV or less at pH on skin. As preferable lipophilic base powders, silicone resin, silicone rubber, silicone resin-covered-silicone rubber, polyamide, polymethyl methacrylate and ethyl carbamate are listed. The zeta-potential of material is not fixed, and it varies according to conditions.

A shape of these lipophilic base powders is not particularly limited. It is generally a spherical, plate-like or indeterminate-like form, and may or may not be porous. It is more preferable that a lipophilic base powder is spherical because particularly light diffusing effect and sense of use become excellent. In particular, when a spherical silicone rubber or spherical silicone resin-covered-silicone rubber is added in skin care cosmetics, agreeable sense of use can be obtained owing to its strongly smooth property.

Although the average primary particle size is not restricted especially, the range of 0.01 to 500 μm is suitable.

In a complex powder of the present invention, plasminogen activator activity inhibiting effect of zinc ion (derived from zinc oxide) is further improved by existence of lipophilic base powder, which adsorbs the plasminogen activator.

In the case of only zinc oxide, concentration of zinc ion must be high in order to inhibit the enzyme sufficiently. So it is sometimes not preferable from a viewpoint of construction of cosmetic preparation.

However, in the case of complex powder of zinc oxide and lipophilic base powder, since lipophilic base powder adsorbs plasminogen activator, zinc ion easily acts on the plasminogen activator. So even concentration of zinc ion is low, plasminogen activator activity inhibiting effect can be exhibited effectively.

When zinc oxide and lipophilic base powder are incorporated separately into a cosmetic, inhibiting effect is slightly higher in some cases. But extremely higher plasminogen activator inhibiting effect is only admitted when complex powder of them is used.

For the reference, trypsin (which is classified to same serine protease as plasminogen activator) is studied. Although trypsin is adsorbed to the complex powder, its activity is hardly lost. In other words, the complex powder of this invention inhibits activity of specific enzyme.

There are two kinds of plasminogen activators called urokinase and tissue form plasminogen activator. The former is recognized in healthy skin and the latter is recognized in disease skin mainly.

The complex powders of this invention are ones that have adsorbing action and blocking action to both of said plasminogen activators.

Complex. Because of its hydrophilic property, zinc oxide powder itself is hardly dispersed in oily base and aggregation generates. About the complex powder of the present invention, it is dispersed in oil well because lipophilic base powder is covered with zinc oxide under specific condition. The definite working modes are explained below.

Complex mode 1. A complex powder in which a covering rate of zinc oxide (14) relative to total surface area of lipophilic base powder (12) is the range of 1 to 90% (FIG. 1 (A)). When a covering rate is over 90%, lipophilicity is not sufficient, and dispersibility in oil is deteriorated in some cases. Further, plasminogen activator adsorbing effect due to lipophilic base powder is not sufficient in some cases. When a covering rate is less than 1%, plasminogen activator activity inhibiting effect due to zinc ion is not sufficiently exhibited in some cases. Therefore, desirable covering rate of zinc oxide is the range of 1 to 90%.

Complex mode 2. A complex powder in which lipophilic base powder (12) is swelling, and a covering rate of zinc oxide (14) relative to total surface area of swollen lipophilic base powder (12) is the range of 1 to 90% at dispersion in oil (FIG. 1 (B)).

Even in the case that a covering rate of zinc oxide relative to total surface area of lipophilic base powder is over 90% at drying state, when a covering rate of zinc oxide relative to a total surface area of a lipophilic base powder is the range of 1 to 90% in the swollen state at dispersion in an oil, better dispersibility in an oil and rough skin recovering/preventing effect are exhibited.

A covering rate used herein is relative to surface area, not to weight.

As swelling lipophilic base powder, silicone resin, silicone rubber, and silicone resin-covered-silicone rubber can be listed. In these powders, whether it swells or not is depends on the condition such as degree of cross-linking.

A hardness of swelling lipophilic base powder is preferably the range of 1 to 80, further preferably the range of 1 to 50. When a hardness is over 80, swelling property is not obtained. On the other hand, the powder with the hardness less than 1 cannot be manufactured.

In this invention, a hardness is measured by Spring method hardness test A type (Japan Industrial Standard K6301).

Spring method hardness test (A type). A spring-type hardness tester (A form) is retained vertical, a press side is contacted so that an indentation needle is vertical to a measuring side of a test piece (thickness 12 mm or larger), and a hardness of a test piece is obtained.

A ratio of average particle diameters of lipophilic base powder and zinc oxide is not particularly limited, but is preferably lipophilic base powder: zinc oxide=1:1 to 10000:1, particularly lipophilic base powder: zinc oxide=5:1 to 1000:1. When zinc oxide is relatively smaller than the aforementioned ratio, there is a tendency that a surface of lipophilic base powder is completely covered, so dispersibility in oil and plasminogen activator adsorbing effect are deteriorated in some cases. In addition, when zinc oxide is relatively larger than the aforementioned ratio, it is difficult to cover lipophilic base powder.

In the present invention, it is necessary that zinc oxide and lipophilic base powder are not simply mixed, but are combined. The complex powder of the present invention is manufactured by mixing zinc oxide and lipophilic base powder by dry process or wet process. A process is not particularly limited as far as it is a process that does not deteriorate the effect of the present invention. For examples, mechanofusion treatment is raised.

Figure 2:
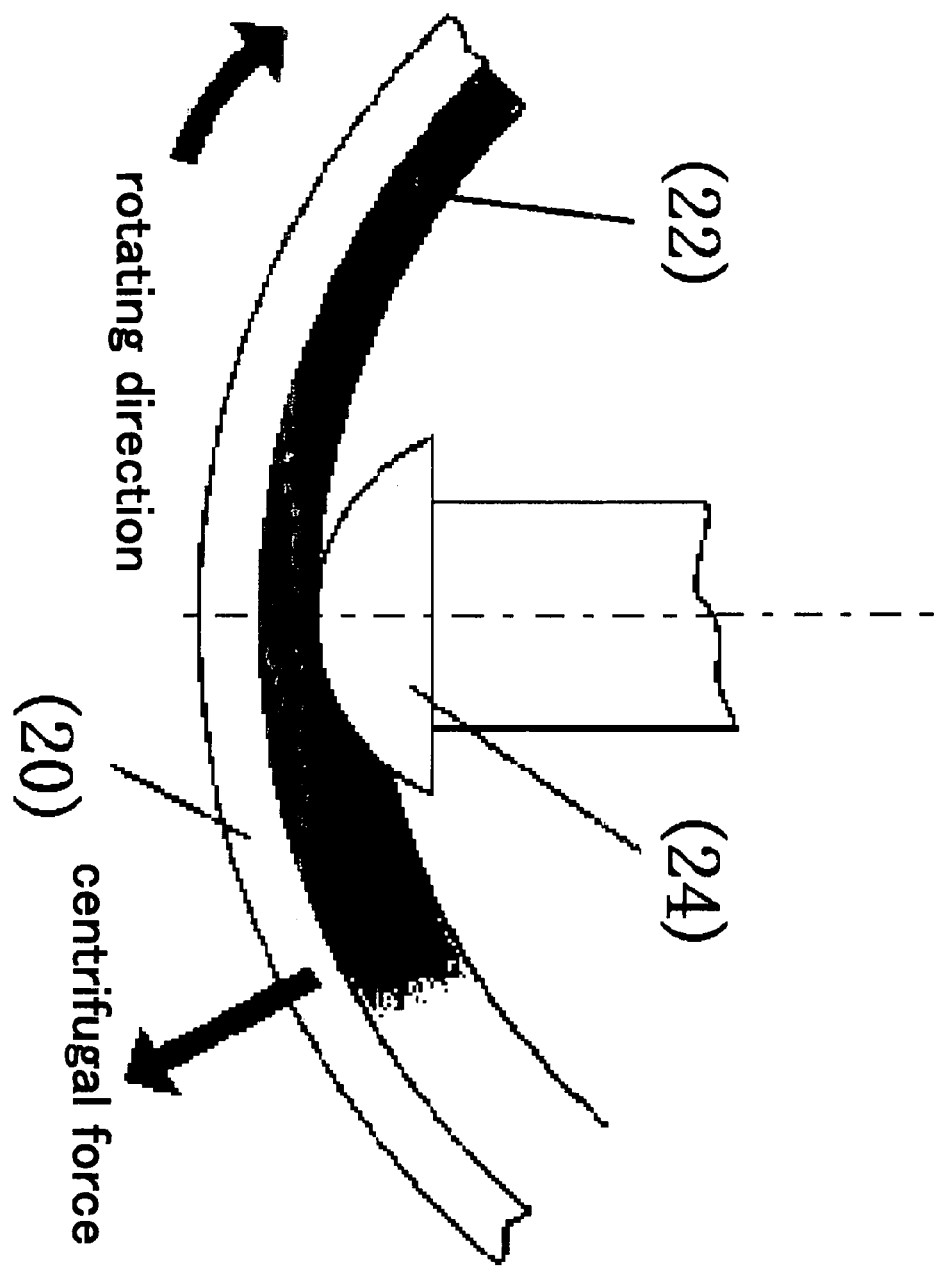
FIG. 2 shows the mechanofusion treatment according to this invention.

Mechanofusion is a technique in which certain mechanical energy is added to different material particles to cause a mechanochemical reaction, thereby a new material is generated. As shown in FIG. 2, powder raw material (22) is placed into a rotating container (20) and fixed at its internal wall by centrifugal force, and taken a strong compression and shear force between the internal wall and an inner piece (24) having different curvature radius. This mechanical procedure is characterized in that a process is simple and a range of combination is remarkably wider in comparison with other procedure such as wet process. The mechanofusion system realizes powder fusion having a higher mixing degree than that of the previous powder mixer, namely not only combining of solid powder due to surface fusion, but also controlling of a shape of a particle.

Besides, many kinds of ball mill, angmill, screen mill, pot mill, mortar, hybridizer and Henschel mixer are applied for mixing apparatus.

The complex powder of the present invention has an appropriate hiding force, so an oily skin external composition incorporating said powder has excellent correcting effect of a spot, a freckle and color ununiformity.

In particular, in the case volatile oil or water is used, easy spreadability on skin and excellent usability are achieved at applying. And after applying, oil or water is volatilized and excellent light diffusing effect on skin is achieved.

In addition, an oily skin external composition incorporating the complex powder of the present invention is excellent in effect of correcting skin irregularity, since said powder is excellent in light diffusing effect. In the case, the shape of lipophilic base powder is spherical, light diffusing effect is particularly excellent.

A content of complex powder in the oily skin external composition of the present invention is not particularly limited as far as the effect of the present invention is obtained. Although the powder can be used appropriately adjusting its amount, but it is generally the range of 1 to 50% by weight, preferably 3 to 20% by weight. In the case, the amount of said powder is smaller than 1% by weight, the effect of the present invention is not sufficiently exhibited. In the case, the amount of said powder is over 50% by weight, it is not preferable from a viewpoint of preparation formulation.

Oil component. Suitable oil components for use in the invention include, without limitation, liquid oil such as avocado oil, camellia oil, turtle oil, macadamia nut oil, corn oil, mink oil, olive oil, rape seed oil, egg yolk oil, sesame oil, par chic oil, wheat germ oil, southern piece oil, castor oil, linseed oil, safflower oil, cotton seed oil, perilla oil, soybean oil, groundnut oil, teaseed oil, Japanese torreya oil, rice bran oil, Chinese wood oil, Japanese paulownia oil jojoba oil, germ oil, triglycerol, avian octane acid glycerol, avian iso palmitic acid glycerol; solid oil such as cacao butter, coconut oil, horse grease, hardening coconut oil, palm oil, beef tallow, sheep grease, hardening beef tallow, palm nucleus oil, lard, cow bone grease, Japan wax nucleus oil, hardened oil, cow foot oil, Japan wax, hardening castor oil; waxes such as bee wax, candelilla wax, cotton wax, carnauba wax, Chinese insect wax, whale wax, montan wax, rice bran wax, lanolin, kapok wax, acetic acid lanolin, liquid crystal lanolin, cane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenation lanolin alcohol ether; hydrocarbon such as liquid paraffin, ozocerite, squalene, pristane, paraffin, ceresin, squalane, vaseline, microcrystalline wax; higher fatty acid such as lauric acid, myristic acid, palmitic acid, stearic acid, behenic acid, oleic acid, undecylenic acid, tall oil acid, isostearic acid, linolic acid, linoleic acid, eicosapentaenoic acid (EPA), docosahexanoic acid (DHA); higher alcohol such as straight chain alcohol (for example, lauryl alcohol, cetyl alcohol, stearyl alcohol, behenic alcohol, myristyl alcohol, oleyl alcohol, cetostearyl alcohol etc.); branched-chain alcohol (for example, monostearyl glycerin ether (batyl alcohol), 2-decyl tetra decynol, lanolin alcohol, cholesterol, phytosterol, hexyl dodecanol, isostearic alcohol, octyl dodecanol); synthesis ester oil such as isopropyl myristate, cetyl octanoate, octyl dodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, dipenta erythritol fatty acid ester, N-alkyl glycol monoisostearate, neopentyl glycol dicapriate, malate diiso stearyl, dipentaerythritol, glycerol di-2-heptul undecanoate, trimethyrol propanetri-2-ethyl hexanoate, trimethyrol propane triiso stearate, pentaerythritol tetra-2-ethyl hexanoate, glycerol tri-2-ethyl hexanoate, glycerol trioctanoate, glycerol triiso palmitate, trimethyrol propane triisostearate, cetyl 2-ethylhexanoate, 2-ethylhexyl palmitate, glycerol trimyristate, glyceride tri-2-heptyl un decanoate, castor oil fatty acid methyl ester, oleyl oleate, acetoglyceride, 2-heptyl undecyl palmitate, diisobutyl adipate, 2-octyldodecyl N-lauroyl L-glutamate, di-2-heptyl undecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate; silicone oil such as chain polysiloxane (for example dimethylpolysiloxane, methyl phenyl polysiloxane, diphenyl polysiloxane etc.), circular polysiloxane (for example octamethyl cyclotetra siloxane, decamethyl cyclopenta siloxane, dodecamethyl cyclohexa siloxane), various kinds of modified polysiloxane (amino modified polysiloxane, polyether modified polysiloxane, alkyl modified polysiloxane, fluorine modified polysiloxane). Especially, silicone oil is used preferably, because it reduces stickiness.

Stimulation relieving effect. When a skin external composition (such as cosmetics) is used, extremely rare person feels stimulation (for example, itching and stinging). When the present complex powder is added to the skin external composition, the above stimulation can be relieved.

Other ingredients. In oily external composition of this invention, other ingredients (for examples other powder components, anionic surfactant, cationic surfactant, ampholytic surfactant, nonionic surfactant, moisturizing agent, water-soluble polymers, thickeners, filmed medicine, ultraviolet absorbent, sequestering agents, lower alcohol, polyalcohol, sugar, amino acids, organic amine, macromolecule emulsion, pH modifier, skin nutrition agents, vitamins, anti-oxidant, antioxidation assistants, perfume and water) which are used in normal cosmetic compositions and pharmaceutical compositions can be appropriately added and said external composition can be manufactured by conventional method.

Further an external composition for skin of the present invention can comprise: a sequestering agents (such as disodium EDTA, trisodium EDTA, sodium citrate, sodium polyphosphate, sodium metaphosphate, gluconic acid and malic acid), caffeine, tannin, verapamil, tranexamic acid and its derivatives, alkylene oxide derivatives, plant extracts (such as glycyrrhiza extract, Chinese quince extract and ichiyakusou extract), medical components (such as tocopherol acetate, glycyrrhezinic acid and its derivatives or salts), whitening agents (such as vitamin C, magnesium ascorbate phosphate, glucoside ascorbate, arbutin, kojic acid), amino acids and its derivatives (such as arginine and lysine), saccharides (such as fructose, mannose, erythritol, trehalose and xylitol), and so on.

In addition, the oily skin external composition of the present invention can be widely applied to a cosmetic, a drug and a quasi-drug that are applied to skin. A dosage form thereof may be any drug formulation form, and can be provided in an arbitrary form such as solution type, solubilized type, emulsion type (O/W type, W/O type, W/O/W type, O/W/O type and so on), water-oil two layers type, gel, aerosol and capsule. In particular, an emulsion type is desirable because elution of zinc ion and extraction of plasminogen activator from skin are easy to happen.

The cosmetic composition is an oily external composition for skin overall, not restricted especially. For example, whitening essence, milky lotion, cream, pack, foundation, lipstick, eye shadow, eye liner, mascara, face wash, body wash, sunscreen cream, foundation, spray, mousse, gel, hair rinse, shampoo, ointment for dermatology and so on, which can be used conventionally as cosmetics.

An external composition of this invention exhibits an excellent effect especially on skin suffering from difficulty in using prior cosmetics (such as sensitive skin).

A sensitive skin is defined in publications as follows: "A skin usually susceptible to damage due to a specific response to materials (such as quasi-drugs, cosmetics, plants, ultraviolet ray and metals) to which most of persons do not respond particularly. A skin which is constitutionally sensitive to an allergenic substances (such as pollen and fragrance) or irritative substances (such as alcohols) due to reduced barrier function." "A skin temporarily susceptible to damage due to an irritating substance when resistance of skin or physiological functions of skin are deteriorated owing to shortage of sleep, overwork, menstruation, turn of seasons, mental stress and the like. A skin having anxiety about the use of cosmetics that is, used routinely."

Thus, decline of skin barrier function, decline of skin irritation threshold, skin dryness, substances causing contact dermatitis, physicochemical irritation, stress, physical condition, seasons change, ultraviolet ray and menstruation are listed as sources for sensitive skin condition. It is possible that one's false skin care itself causes a sensitive skin. Or even in the case that one is only obsessed by the idea of being sensitive skin, it is also classified to sensitive skin.

As used herein, a subject having a sensitive skin is defined as one who experiences abnormal felling in any of the procedures (1) to (5) shown below.

(1) 100 µl of 5% citric acid solution is applied over cheek and left for 10 minutes.

(2) 100 µl of 5% lactic acid solution is applied over cheek and left for 10 minutes.

(3) 100 µl of 50% ethanol solution is applied over cheek and left for 10 minutes.

(4) An unwoven fabric (2×2 cm) is immersed with 100 µl of 0.2% methyl paraben solution, applied over cheek and left for 10 minutes.

(5) An unwoven fabric (2×2 cm) is immersed with 100 µl of 5% SDS solution, applied over cheek and left for 10 minutes.

The abnormal felling means relatively painful feeling on skin, such as stingy pain, irritating sensation, itching sensation, burning sensation, discomfort, pricking pain and the like.

In the following, the present invention is explained by using specific examples. However, the present invention should not be restricted thereto.

Complex powder 1. Zinc oxide covering silicone rubber powder (swelling type). Zinc oxide (zinc white SEIDO: average particle size 0.5 µm) and silicone rubber powder (Trefil E506W™:zeta-potential −12.0 mV: average particle size 5 µm) are mixed by various mixing ratio, and combined by mechanofusion treatment (2600 rpm, 2 minutes) to obtain complex powders having desired covering rate. (complex powder 1-1 to 1-6).

A covering rate of zinc oxide relative to total surface area of silicone rubber powder at swelling is observed by electron microscope.

TABLE 3

| | Complex powder | | | | | |
|---|---|---|---|---|---|---|
| | 1-1 | 1-2 | 1-3 | 1-4 | 1-5 | 1-6 |
| Covering rate at swelling (%) | 1 | 5 | 10 | 50 | 90 | 100 |

Comparative powder 1: Mixture of zinc oxide (Zinc white SEIDO: average particle size 0.5 µm) and silicone rubber powder (Trefil E506W ™) (weight ratio 1:9)

Confirm of complex. In order to confirm the fact that the complex powder of the present invention is not simply mixed but is combined, the following test is performed. When 0.1 g of complex powder 1-3, 20 g of water and 20 g of silicone oil (Silicone oil D5™) are mixed with stirring, said powder is well dispersed in oily phase. Similarly, when 0.1 g of mixed powder of comparative powder 2, 20 g of water and 20 g of silicone oil (Silicone oil D5™) are mixed with stirring, a silicone rubber powder is dispersed in oily phase and zinc oxide is dispersed in water phase separately. From this fact, it is demonstrated that zinc oxide and lipophilic base powder are not simply mixed but are combined in the present invention.

Next, using complex powders 1-3 and comparative powders 1, 2 and 3, dispersibility in oil and rough skin recovering effect are tested. The concrete test method and criterion are as follows.

Dispersibility in Oil of Powder.
(Test method). Powder and silicone oil (Silicone oil D5™) are mixed with stirring.
(Criterion)
○: Dispersed satisfactory
X: Aggregated Rough Skin Recovering Effect.
(Test method). According to formulations of the following Table 4, oily skin external compositions are prepared. Using faces of 20 panelists, said compositions are applied once or more times per day for 8 weeks, thereafter the states of skin are assessed.

Remarkably effective: Skin condition became good remarkably.
Effective: Skin condition became good.
Some effective: Skin condition became good slightly.
Ineffective: Skin condition was not changed, or deteriorated.
(Criterion)
◎: Proportion that the test subject showing remarkably effective, effective and some effective (effective rate) is 80% or more,
○: The effective rate is 50% or more less than 80%
Δ: The effective rate is 30% or more less than 50%
X: The effective rate is less than 30%

TABLE 4

| (1) Test powder | 6.0 |
|---|---|
| (2) Dimethylpolysiloxane | 20.0 |
| (3) Lanolin | 5.0 |
| (4) Stearyl alcohol | 4.0 |
| (5) Bee wax | 3.0 |
| (6) Stearic monoglyceride | 2.0 |
| (7) P.O.E(20 mol)Sorbitan monooleate | 2.0 |
| (8) 1,3-butylene glycol | 5.0 |
| (9) Glycerin | 5.0 |
| (10) Purified water | remainder |

The process. Components (1) to (7) are heated and kept at 75° C. (oil phase), Components (8) and (9) are dissolved in components (10), and heated to 75° C. (water phase). The water phase is added to the oil phase and emulsified by homomixer, and then cooled to 30° C. while agitating well Complex powder 1-3: 10% Zinc oxide covering silicone rubber powder.
Comparative powder 1: Mixture of zinc oxide (zinc white SEIDO: average particle size 0.5 µm) and silicone rubber powder (Trefil E506W™) (weight ratio 1:9).
Comparative powder 2: Silicone rubber powder (Trefil E506W™)
Comparative powder 3: Zinc oxide (zinc white SEIDO: average particle size 0.5 µm). The result is shown in Table 5.

TABLE 5

| | Complex powder | Comparative powder | | |
|---|---|---|---|---|
| | 1-3 | 1 | 2 | 3 |
| Dispersibility in oil | ○ | X | ○ | X |
| Rough skin recovering effect | ◎ | Δ | X | Δ |

Since zinc oxide has hydrophilic character, dispersibility in oil and rough skin recovering effect are low in the case of zinc oxide alone (Comparative powder 3). In the case of silicone rubber powder alone, although dispersibility in oil is better, rough skin recovering effect is not obtained (Comparative powder 2). In addition, when zinc oxide and lipophilic base powder are incorporated separately, rough skin recovering effect is not sufficient (Comparative powder 1). To the contrary, in the case of complex powder of the present invention, both of dispersibility in oil and rough skin recovering effect are excellent.

Thereby in the complex powder of the present invention, it is confirmed that plasminogen activator activity inhibiting effect of zinc ion derived from zinc oxide is further improved by the presence of lipophilic base powder that adsorbs the plasminogen activator. Further, it is confirmed that extremely higher rough skin recovering effect is recognized in these complex powders in comparison with the case zinc oxide and lipophilic base powder are incorporated separately.

Complex powder 2. Zinc oxide covered silicone resin covered silicone rubber powder. According to the same procedure as that of Complex powder 1 [except that a silicone resin-covered silicone rubber powder (KSP100™: zeta-potential −14.0 mV: average particle diameter 5 μm) is used in place of silicone rubber powder], complex powders with desired covering rate are obtained. A complex powder (covering rate: 10%) is named complex powder 2-1, and a complex powder (covering rate: 50%) is named complex powder 2-2.

Comparative powder 4: Silicone resin-covered-silicone rubber powder (KSP100™)

Comparative powder 5: Mixture of zinc oxide (zinc white SEIDO: average particle size 0.5 μm) and silicone resin-covered-silicone rubber powder (KSP100™) (weight comparison 1:9).

Next using oily external composition for skin containing the above powders, the rough skin recovering effect is tested. The prescription of oily external composition for skin is shown in Table 4.

Rough Skin Preventing Effect.
(Test method). An absorbent cotton (2 2 cm) immersed with 5% SDS solution is applied to two places of forearm inner part of 54 male panelists and fixed for 15 minutes, an active agent is washed out, and an oily skin external composition assigned to each panelist is applied thereon (n=3). This procedure is repeated for 7 days, a test part is sufficiently washed and left 60 minutes. A degree of rough skin induced by SDS is observed, and a score is subjected based on the following criterion. A non-applied part is adopted as a control part. Further, a difference in score between a control part and a sample-applied part is obtained every panelist, summed each sample, and effect of each sample is determined based on the following rough skin preventing effect criteria.
(Marks Standard of Skin Roughness).
Marks 4: Erythema and/or desquamation is admitted clearly.
Marks 3: Erythema and/or desquamation is admitted middle degree.
Marks 2: A little erythema and/or fissure of horny layer is admitted.
Marks 1: A horny layer surface looks whitish or powder-coated.
Marks 0: No symptom.
(Criterion of Rough Skin Preventing Effect)
◎=Clearly effective: mark difference is 6 or more.
○=A little effective: mark difference is 4 or 5.
Δ=Tend to prevent: mark difference is 2 or 3.
X=No effect: mark difference is 1 or less.
The result is shown in Table 6.

|  | Complex powder | | Comparative powder | |
| --- | --- | --- | --- | --- |
|  | 2-1 | 2-2 | 4 | 5 |
| Rough skin preventing effect | ◎ | ◎ | X | Δ |

In the case of lipophilic base powder alone (Comparative powder 4) and in the case where zinc oxide and lipophilic base powder are incorporated without complexing (Comparative powder 5), little effect are seen in comparison with non-applying part. To the contrary, in the case where the complex powder of the present invention (Complex powder 2-1, 2-2) is incorporated, the effect is clearly seen.

It is confirmed that, in the complex powder of the present invention, extremely high rough skin preventing effect is achieved by combining zinc oxide and lipophilic base powder.

Complex Powder 3. Zinc Oxide Covering Polyamide Powder.

According to the same procedure as that of Complex powder 1 [except that a polyamide powder (Nylon SP500™: zeta-potential −32.0 mV: average particle size 5 μm) is used in place of a silicone rubber powder], complex powders with desired covering rate are obtained.

Complex Powder 4. Zinc Oxide Covering Polyethylene Powder.

According to the same procedure as that of Complex powder 1 [except that a polyethylene powder (Flo-thene UF™: zeta-potential +1.0 mV: average particle size 5 μm) is used in place of a silicone rubber powder], complex powders with desired covering rate are obtained.

Relation among zeta-potential of lipophilic base powder, dispersibility in oil and rough skin recovering effect of complex powder.

Using 10% zinc oxide covered lipophilic base powder, a relationship among zeta-potential of lipophilic base powder, dispersibility in oil and rough skin recovering effect of complex powder is tested. The concrete test method and the criterion are as the above mentioned. The result is shown in Table 7.

TABLE 7

|  | Complex powder | | | |
| --- | --- | --- | --- | --- |
| Complex powder | 1-3 | 2-1 | 3 | 4 |
| Lipophilic base powder | *1 | *2 | *3 | *4 |
| Zeta-potential(mv) | −12.0 | −14.0 | −32.0 | +1.0 |
| Covering rate(%) | 10 | 10 | 10 | 10 |
| Dispersibility in oil | ○ | ○ | ○ | ○ |
| Rough skin recovering effect | ◎ | ◎ | ◎ | Δ |

*1: Silicone rubber
*2: Silicone resin covering silicone rubber
*3: Polyamide
*4: Polyethylene All complex powders are well dispersed in oil. But in the case of polyethylene (zeta-potential is positive value), rough skin recovering effect is not sufficient. While in the cases of silicone rubber, polyamide and silicone rubber covering silicone resin (zeta-potential is negative value), rough skin recovering effect is remarkably excellent. This is because since lipophilic base powder having a negative zeta-potential adsorbs plasminogen activator, zinc ion easily acts on the plasminogen activator and exerts inhibiting effect. Therefore, it is desirable that zeta-potential of lipophilic base powder is negative value, especially −10 mV or below.

Relation among zinc oxide covering rate, dispersibility in oil and rough skin recovering effect of complex powder. Then, using zinc oxide covering lipophilic base powders of the complex powders 1 and 3, a relationship among zinc oxide covering rate, dispersibility in an oil and rough skin recovering effect of complex powder is tested. The result is shown in Table 8 and 9.

TABLE 8

Zinc oxide covering silicone rubber powder (swelling)

| | Complex powder | | | | | |
|---|---|---|---|---|---|---|
| | 1-1 | 1-2 | 1-3 | 1-4 | 1-5 | 1-6 |
| Covering rate (%) | 1 | 5 | 10 | 50 | 90 | 100 |
| Dispersibility in oil | ○ | ○ | ○ | ○ | ○ | X |
| Rough skin recovering effect | ○ | ◎ | ◎ | ◎ | ○ | Δ |

TABLE 9

Zinc oxide covering polyamide powder

| | Complex powder | | | | | |
|---|---|---|---|---|---|---|
| | 3-1 | 3-2 | 3-3 | 3-4 | 3-5 | 3-6 |
| Covering rate(%) | 1 | 5 | 20 | 50 | 90 | 100 |
| Dispersibility in oil | ○ | ○ | ○ | ○ | ○ | X |
| Rough skin recovering effect | ○ | ◎ | ◎ | ◎ | ○ | Δ |

It is confirmed from Table 9 that, when zinc oxide covering rate is the range of 1 to 90%, both of dispersibility in oil and rough skin recovering effect are excellent. When covering rate is over 90%, since zinc oxide covers lipophilic base powder without interspace, lipophilic base powder cannot contact with oil. So dispersibility in oil is inferior and the surface cannot adsorb an enzyme, resulting in inferior rough skin recovering effect.

When lipophilic base powder is silicone rubber (swelling type), covering rate of zinc oxide at drying may be over 90%. This is because silicone rubber is swollen at dispersion in oil and a covering rate is reduced consequently. It is confirmed from Table 8 that both of dispersibility in oil and rough skin recovering effect are excellent, when covering rate at swelling is the range of 1 to 90%.

Improvement effect of optical characteristics. In the process of evaluating about complex powder, the inventors found out that oily external composition for skin of this invention has an excellent improvement effect about optical characteristics.

That is, in the case of oily skin external composition of the present invention (in particular, when spherical resin powder is used as base powder), skin color ununiformity hiding effect and irregularity shading off effect are remarkably improved, so appearance of skin is improved.

Using silicone oil swelling base powder (one kind of spherical resin powder), sense of use is especially excelled. As silicone oil swelling base powder, silicone rubber powder and silicone resin covered-silicone rubber powder can be raised. Regarding this point, the inventors evaluate as follows. In the following evaluation, the powder part of the following basic prescription is substituted.

TABLE 10

| Basic prescription | |
|---|---|
| Water | 59 |
| Dimethylpolysiloxane (20 cs) | 25 |
| Crosslinking polyether modified silicone | 10 |
| Powder | 6 |

Furthermore, the crosslinking polyether modified silicone used in this working mode has the following structure. The crosslinking polyether modified silicone is premixed with dimethylpolysiloxane.

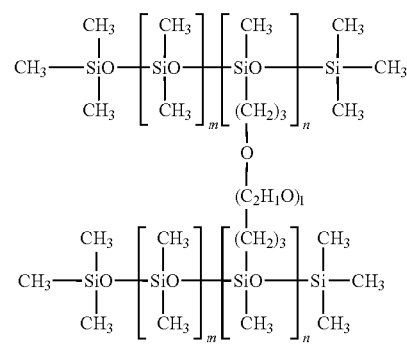

(In the above constitutional formula, 1 is 3 to 20, m is 10 to 200, n is 1 to 10.)

Also, evaluation is carried out on the basis of the following standard.

[Sense of use] and [Absence of powdery feeling]: Mainly assessed by feeling at applying on skin.
[Not falling in skin texture and skin pore]: Mainly assessed by inhibiting effect of the following phenomenon; pigment powder falls into skin pore or fine crease part, and the presence of skin texture and skin pore is conspicuous by light and shade of pigment color.
[Color ununiformity hiding effect]: Assessed by effect of hiding color ununiformity (such as fine spots on skin).
[Irregularity shading effect]: Assessed by effect of shading irregularities (such as pores and fine creases on skin).
[Translucent and naturalness]: Mainly assessed by whether translucent of skin is lost or not.
[Attractiveness of skin]: Assessed by overall organoleptic evaluation.

TABLE 11

| | Test example | | | |
|---|---|---|---|---|
| | 5-1 | 5-2 | 5-3 | 5-4 |
| Spherical silicone rubber powder | 6 | — | — | 4.98 |
| Complex powder | — | 6 | — | — |
| Zinc white | — | — | 6 | 1.02 |
| Powder total | 6 | 6 | 6 | 6 |
| Sense of use | ◎ | ◎ | X | ○ |
| Absence of powdery feeling | ◎ | ◎ | X | ○ |
| Not falling in skin texture and skin pore | ◎ | ◎ | X | Δ |
| Color ununiformity hiding effect | X | ○ | ○ | Δ |
| Irregularity shading effect | ○ | ◎ | X | Δ |
| Translucent and naturalness | ◎ | ◎ | X | ○ |
| Attractiveness of skin | ○ | ◎ | X | Δ |

As apparent from the above Table 11, when spherical silicone rubber powder is used (Test example 5-1), sense of use as characteristic inherent to powder is extremely better, and a powder itself has high transparency and relatively low refractive index (about 1.4), so texture and skin pore falling and transparent feeling are also excellent. But color ununiformity hiding effect is not satisfactory.

On the other hand, when zinc white is used (Test example 5-3), color ununiformity hiding effect is better due to its high hiding degree, but sense of use is worse and zinc white falls into fine concave part such as skin pore, and concave part looks floating white.

To the contrary, when complex powder in which spherical silicone rubber powder (lipophilic base powder) covered with zinc white (17% by weight) is used (Test example 5-2), it is confirmed that color ununiformity hiding effect and irregularity shading out effect are improved.

Spherical silicone rubber powder and zinc white are incorporated separately at the same weight ratio as that of complex powder of Test example 5-4, optical property is greatly deteriorated. Namely the effect of improving optical property is obtained by combining.

Then, the present inventors study a relationship among zinc white covering rate in complex powder, nature of base powder and optical property.

TABLE 12

| | Test example | | | |
|---|---|---|---|---|
| | 5-6 | 5-7 | 5-8 | 5-9 |
| Complex powder(5%) | 6 | — | — | — |
| Complex powder(17%) | — | 6 | — | — |
| Complex powder(30%) | — | — | 6 | — |
| Complex powder (non-swelling) | — | — | — | 6 |
| Powder total | 6 | 6 | 6 | 6 |
| Sense of use | ◎ | ◎ | ◎ | ◎ |
| Absence of powdery feeling | ◎ | ◎ | ◎ | ○ |
| Not falling in skin texture and skin pore | ◎ | ◎ | ◎ | ◎ |
| Color ununiformity hiding effect | ○ | ○ | ◎ | ○ |
| Irregularity shading effect | ○ | ◎ | ◎ | ◎ |
| Translucent and naturalness | ◎ | ◎ | ◎ | ◎ |
| Attractiveness of skin | ○ | ◎ | ◎ | ◎ |

Until about 30%, a weight ratio of zinc white in complex powder has a tendency that optical property is improved as covering rate is increased.

In addition, when non-swelling spherical nylon powder is used as base powder of complex powder, there is a tendency that sense of use is slightly decreased, but there is no great influence on optical property (Test example 5-9: Covering quantity 17%).

As described above, according to the oily skin external composition of the present invention (in particular, when spherical powder is used as base powder), not only rough skin recovering/preventing effect but also excellent effect of improving optical property of skin is recognized. In addition, when complex powder having a low covering rate is used, color ununiformity hiding effect can be enhanced by combining high refractive index powder such as titanium oxide.

Stimulation relieving test. Stimulation at applying to skin is assessed. Using extremely rare 10 subjects who feel stimulation (such as itching and stinging) upon applying of skin external composition shown in Table 16, a stimulation relieving test is performed.

TABLE 16

| (1) Dimethylpolysiloxane | 20.0 |
|---|---|
| (2) Lanolin | 5.0 |
| (3) Stearyl alcohol | 4.0 |
| (4) Bee wax | 3.0 |

TABLE 16-continued

| (5) Stearic acid monoglyceride | 2.0 |
|---|---|
| (6) P.O.E(20 mol) Sorbitan monooleate | 2.0 |
| (7) 1,3-Butylene glycol | 5.0 |
| (8) Glycerin | 5.0 |
| (9) Methyl paraben | 0.2 |
| (10) Purified water | remainder |

(The process). Components (1) to (6) are heated and kept at 75° C. (oil phase). Components (7), (8) and (9) are dissolved in components (10) and heated 75° C. (water phase). The water phase is added to the oil phase, emulsified with homomixer and cooled to 30° C. while mixing well.

Blending 6% by weight of each powder in the external composition for skin of the above Table 16, stimulation relieving effect is tested.

Complex powder 1-3: 10% Zinc oxide covering silicone rubber powder. Comparative powder 1: Mixture of zinc oxide (zinc white SEIDO: average particle size 0.5 µm) and silicone rubber powder (Trefil E506W™) (weight comparison 1:9).

Comparative powder 2: Silicone rubber powder (Trefil E506W™).

Comparative powder 3: Zinc oxide (zinc white SEIDO: average particle size 0.5 µm).

Evaluation standard of stimulation relieving effect

◎=Effective: Less than 6 persons felt stimulation.

○=Some effective: 7 or 8 persons felt stimulation.

Δ=Slightly effective: 8 or 9 persons felt stimulation.

X=Ineffective: 10 persons felt stimulation.

TABLE 17

| | Test example | | |
|---|---|---|---|
| 7-1 | 7-2 | 7-3 | 7-4 |
| Complex powder | Comparative powder | | |
| 1-3 | 1 | 2 | 3 |
| ◎ | X | X | Δ |

It is confirmed that the stimulation is suppressed by blending complex powder of this invention.

The suitable blending example of this invention is shown below. This invention is not restricted by these examples.

| Blending example 1 Cream | |
|---|---|
| (The prescription) | (% by weight) |
| 1) Monoglyceryl stearate | 2.0 |
| 2) Stearyl alcohol | 4.0 |
| 3) Bee wax | 3.0 |
| 4) Lanolin | 5.0 |
| 5) P.O.E (20 mol)sorbitan monooleate | 2.0 |
| 6) Squalane | 20.0 |
| 7) Zinc oxide covering silicone rubber powder | 5.0 |
| 8) Perfume | 0.2 |
| 9) 1,3-Butylene glycol | 5.0 |
| 10) Glycerol | 5.0 |
| 11) Purified water | remainder |

The process. Components 1 to 8 are heated and keep at 75° C. (oil phase). Components 9 and 10 are dissolved in 11 and warmed to 75° C. (water phase). The water phase is added to the oil phase and emulsified by homomixer homogeneously and cooled to 30° C. while agitating well.

Blending example 2. Emulsifying foundation.

| (The prescription) | (% by weight) |
|---|---|
| 1) Stearic acid | 0.4 |
| 2) Isostearic acid | 0.3 |
| 3) Cetyl 2-ethyl hexanoate | 4.0 |
| 4) Liquid paraffin | 11.0 |
| 5) P.O.E(10) Stearyl ether | 2.0 |
| 6) Talc | 15.0 |
| 7) Red iron oxide | 0.01 |
| 8) Yellow iron oxide | 0.001 |
| 9) Black iron oxide | 0.05 |
| 10) Cetyl alcohol | 0.3 |
| 11) Zinc oxide covering polyamide powder | 5.0 |
| 12) Triethanolamine | 0.4 |
| 13) Dipropylene glycol | 5.0 |
| 14) Perfume | 0.01 |
| 15) Purified water | remainder |

The process. After components 1 to 10 are heated and dissolved at 85° C., component 11 is added thereto and dispersed uniformly.

A mixture (components 12, 13 and 15 are heated and dissolved at 85° C.) is gradually added thereto and emulsified. After maintaining an emulsification temperature for 10 minutes with stirring, the material is cooled to 45° C. while stirring. Component 14 is added thereto, cooled to 35° C. while stirring, and filled in a container.

Blending example 3. W/O type emulsifying makeup foundation.

| (The prescription) | (% by weight) |
|---|---|
| 1) Cyclomethylsilicone | 30.0 |
| 2) Dimethylsilicone | 2.0 |
| 3) Silicone resin | 1.0 |
| 4) Antioxidant | proper quantity |
| 5) Octyl methoxycinnamate | 3.0 |
| 6) 4-Tert buthyl-4'-methoxy benzoyl methane | 1.0 |
| 7) Isostearic acid | 1.0 |
| 8) Silicone treated alumina | 8.0 |
| 9) Cation modified bentonite | 2.0 |
| 10) Zinc oxide covering silicone resin powder | 5.0 |
| 11) Talc | 5.0 |
| 12) Spherical PMMA resin powder | 5.0 |
| 13) Purified water | remainder |
| 14) Glycerin | 4.0 |
| 15) 1,3-Propylene glycol | 1.0 |
| 16) Stabilizer | proper quantity |
| 17) Perfume | proper quantity |

The process. Components 1-9, 12, 16 and 17 are heated and dissolved at 85° C., and components 10 and 11 are added thereto and dispersed (oil phase). Components 14 and 15 are added to component 13 and dispersed homogeneously (water phase).

The oil phase is added in the water phase with stirring and kept 85° C. for 100 minutes, and then cooled to 45° C. with stirring.

Blending example 4. W/O type emulsifying foundation.

| (The prescription) | (% by weight) |
|---|---|
| 1) Silicone treated synthesis mica | 15.0 |
| 2) Silicone treated sericite | 7.0 |
| 3) Silicone treated titanium oxide | 12.0 |
| 4) Silicone treated red Iron oxide | 1.2 |

-continued

Blending example 4. W/O type emulsifying foundation.

| (The prescription) | (% by weight) |
|---|---|
| 5) Silicone treated yellow Iron oxide | 2.3 |
| 6) Silicone treated black Iron oxide | 0.6 |
| 7) Zinc oxide covering silicone rubber powder | 12.0 |
| 8) Spherical PMMA powder | 4.0 |
| 9) Cyclomethicone | remainder |
| 10) Dimethylpolysiloxane | 4.0 |
| 11) Squalane | 3.0 |
| 12) Polyether modified silicone | 2.0 |
| 13) Sorbitan sesuqui isostearate | 1.0 |
| 14) Co-dispersion | proper quantity |
| 15) Dipropylene glycol | 2.0 |
| 16) Phenoxyethanol | 0.1 |
| 17) Purified water | 20.0 |
| 18) Antioxidant | proper quantity |
| 19) Perfume | proper quantity |

The process. Components 1-14 are heated and dissolved at 85° C. (oil phase). Component 16 is added to component 17 and dispersed homogeneously (water phase). The oil phase is added in the water phase with stirring and kept 85° C. for 100 minutes, added components 18 and 19, and then cooled to 45° C. with stirring.

Blending example 5. Stick foundation.

| (The prescription) | (% by weight) |
|---|---|
| 1) Titanium oxide | 13.0 |
| 2) Kaolin | 12.0 |
| 3) Zinc oxide covering silicone resin covering silicone rubber powder | 13.7 |
| 4) Red iron oxide | 1.0 |
| 5) Yellow iron oxide | 0.7 |
| 6) Black iron oxide | 0.1 |
| 7) Squalane | 37.0 |
| 8) Cetyl 2-ethyl hexanoate | 16.0 |
| 9) Sorbitan sesquioleate | 1.0 |
| 10) Microcrystalline wax | 4.0 |
| 11) Carnauba wax | 1.3 |
| 12) Perfume | 0.2 |

The process. Components 7-9 are mixed at 80° C., components 1-6 are added thereto, and this is mixed with disbar and subjected to TK mill treatment. Further, components 10 and 11 (which are heated and dissolved) are added thereto and degassed. After component 12 is mildly mixed therein, this is filled into a container at 80° C. and cooled.

Blending example 6. Oily eye shadow.

| (The prescription) | (% by weight) |
|---|---|
| 1) Dimethicone | 10.0 |
| 2) Ester oil | 10.0 |
| 3) Liquid paraffin | remainder |
| 4) Squalane | 10.0 |
| 5) Sorbitan sesuqui isostearate | 1.0 |
| 6) Polyethylene wax | 8.0 |
| 7) Ceresin wax | 3.0 |
| 8) Mica | 7.0 |
| 9) Spherical cellulose powder | 5.0 |
| 10) Mica titanium | 8.0 |
| 11) Zinc oxide covering silicone rubber powder | 7.0 |
| 12) Kaolin | 10.0 |
| 13) Antioxidant | proper quantity |
| 14) Perfume | proper quantity |

The process. Components 1-7 are heated and dissolved at 85° C., components 8-12 are added thereto with stirring, and components 13 and 14 are added with stirring. After that it is filled into a container and cooled.

Blending example 7. Lipstick.

| (The prescription) | (% by weight) |
|---|---|
| 1) Polyethylene wax | 10.0 |
| 2) Ceresin wax | 3.0 |
| 3) Lanolin | 20.0 |
| 4) Polybutene | 20.0 |
| 5) Octyl methoxycinnamate | 5.0 |
| 6) Dimethicone | 12.0 |
| 7) Ester oil | remainder |
| 8) Titanium oxide | 4.5 |
| 9) Red 201 | 0.5 |
| 10) Red 202 | 1.1 |
| 11) Red 223 | 0.3 |
| 12) Spherical Polyethylene powder | 3.0 |
| 13) Red iron oxide covering mica titanium | 12.0 |
| 14) Zinc oxide covering silicone rubber powder | 5.0 |
| 15) Boron nitride powder | 5.0 |
| 16) Antioxidant | proper quantity |
| 17) Perfume | proper quantity |

The process. Components 1-7 are heated and dissolved at 85° C., components 8-15 are added thereto with stirring, and components 16 and 17 are added thereto with stirring. After that it is filled into a container and cooled.

Blending example 8. Cream.

| (The prescription) | (% by weight) |
|---|---|
| 1) Zinc oxide covering silicone resin covering silicone rubber powder | 5.0 |
| 2) Polyether modified silicone | 1.5 |
| 3) Decamethyl cyclopenta siloxane | 26.0 |
| 4) Dimethylpolysiloxane | 3.0 |
| 5) Purified water | remainder |
| 6) Paraben | 0.15 |
| 7) Dynamite glycerol | 7.0 |
| 8) 1,3-Butylene glycol | 7.0 |
| 9) Stabilizer | proper quantity |
| 10) Perfume | proper quantity |

The process. Components 2-4 are mixed, component 1 is added therein and dispersed (oil phase). Components 5-10 are heated with stirring (water phase). The water phase is added in the oil phase and emulsified.

Blending example 9. Cream.

| (The prescription) | (% by weight) |
|---|---|
| 1) Cyclomethicone | 16 |
| 2) Cross linking polyether modified silicone | 1 |
| 3) Polyether modified silicone | 1 |
| 4) Olefin oligomer | 2 |
| 5) Cetyl 2-ethyl hexanoate | 0.5 |
| 6) Tocopherol acetate | 0.05 |
| 7) Purified water | remainder |
| 8) Sodium citrate | 0.03 |
| 9) Citric acid | 0.07 |
| 10) Sodium chloride | 1 |
| 11) Polyethylene glycol 6000 | 1 |
| 12) Concentrated glycerin | 8 |
| 13) Dipropylene glycol | 3 |
| 14) Ethanol | 3 |
| 15) Sodium carboxymethylcellulose | 0.25 |
| 16) 1,3-butylene glycol | 2 |

Blending example 9. Cream. -continued

| (The prescription) | (% by weight) |
|---|---|
| 17) Antiseptics | proper quantity |
| 18) Zinc oxide covering silicone rubber powder | 5 |
| 19) Hydrophobicized titanium oxide | 1 |

The process. An oily phase mixture is prepared as follows; component 6 is dissolved in component 5, and this is added to a mixture of components 1-4. A water phase mixture is prepared as follows; components 8-13 are successively added to component 7, and a substance (component 15 is wetted in component 14) and other substance (component 17 is heated and dissolved in component 16) are added therein. An objective cream is obtained as follows; a water phase mixture is added to an oily phase mixture while stirring using high speed mixer, and components 18 and 19 are added therein using high speed mixer.

All of the aforementioned oily external compositions for skin have excellent rough skin recovering/preventing effect, and dispersibility of powder in oil was better.

In addition, the aforementioned oily external compositions for skin are excellent in effect of correcting spots, freckles and color ununiformity, and have no skin stimulating property.

What is claimed is:

1. An oily external composition for skin comprising:
   a complex powder including lipophilic base powder and zinc oxide, where the surface of lipophilic base powder is covered with zinc oxide; and an oil component;
   wherein said complex powder is dispersed and swelled in said oil component,
   wherein the zeta-potential of said lipophilic base powder is a negative value at pH 7.5, and
   wherein the zinc oxide covers from 5 to 50% of the total surface area of said lipophilic base powder dispersed in said oil component, and
   wherein the lipophilic base powder is one or more selected from the group consisting of silicone resin, silicone rubber, and silicone resin-covered-silicone rubber.

2. The oily external composition for skin according to claim 1 wherein the oil component comprises silicone oil.

3. The oily external composition for skin according to claim 1 wherein the content of said complex powder is in the range of 1 to 50% by weight.

4. The oily external composition for skin according to claim 1 wherein said composition is an emulsion.

5. A method of treating rough skin comprising:
   applying the composition of claim 1 to rough skin to thereby promote recovering of said rough skin.

6. A method of treating sensitive skin comprising:
   applying the composition of claim 1 to sensitive skin to thereby relieve an abnormal feeling associated with said sensitive skin.

7. A complex powder comprising a lipophilic base powder and zinc oxide, wherein the surface of said lipophilic base powder is covered with zinc oxide, wherein the zeta-potential of said lipophilic base powder is a negative value at pH 7.5, wherein zinc oxide covers 5 to 50% of the total surface area of said lipophilic base powder when said lipophilic base powder is dispersed and swelled in oil and wherein the lipophilic base powder is one or more selected from the group consisting of silicone resin, silicone rubber, and silicone resin-covered-silicone rubber.

* * * * *